United States Patent
Sunaga et al.

(10) Patent No.: US 6,342,568 B1
(45) Date of Patent: *Jan. 29, 2002

(54) METALLOCENE COMPOUND, AND PROCESS FOR PREPARING POLYOLEFIN BY USING IT

(75) Inventors: Tadahiro Sunaga, Kanagawa; Kenji Michiue; Masahiro Yamashita, both of Hiroshima; Yukio Ishii, Osaka, all of (JP)

(73) Assignee: Mitsui Chemicals, Inc. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/300,289

(22) Filed: Apr. 27, 1999

(30) Foreign Application Priority Data

May 6, 1998 (JP) ............................................. 10-123576

(51) Int. Cl.[7] ............................ C08F 4/44; C07F 17/00; C07F 7/00; B01J 31/00
(52) U.S. Cl. ........................... 526/160; 556/11; 556/12; 556/53; 502/103; 502/117; 526/351; 526/943
(58) Field of Search .............................. 556/11, 12, 53; 502/103, 117; 526/160, 943, 351

(56) References Cited

U.S. PATENT DOCUMENTS 5,571,880 A * 11/1996 Alt et al. .................... 526/160

FOREIGN PATENT DOCUMENTS

| EP | 0610843 A | 8/1994 |
|----|-----------|--------|
| EP | 0666267 A | 8/1995 |
| JP | 1-501950 | 7/1989 |
| JP | 1-502036 | 7/1989 |
| JP | 3-193797 | 8/1991 |
| JP | 3-212408 | 9/1991 |
| JP | 4-69394 | 3/1992 |
| JP | 4-85310 | 3/1992 |
| JP | 4-268307 | 9/1992 |
| JP | 5-170822 | 7/1993 |
| JP | 9-309911 | 12/1997 |
| WO | 9215596 A | 9/1992 |

OTHER PUBLICATIONS

Helmut G. Alt et al., "Syndiospecific polymerization of propylene: new metallocene complexes of type $(C_{13}H_{8-n}R_nCR'R''C_5H_4)MCl_2$ (n=0,2; R=Alkyl, Aryl, Hal; R', R''=H, Alkyl, Aryl; M=Zr, Hf) with special regard for different bridge substituents" J. Organomet. Chem. (1996) 518 (1–2), 7–15.

Helmut G. Alt et al., "Cl–Bridged fluorenylidene cyclopentadienylidene complexes of the type $(C_{13}H_8-CR^1R^2-C_5H_3R)ZrCl_2$ ($R^1$, $R^2$–alkyl, phenyl, alkenyl; R–H, alkyl, alkenyl, substituted silyl) as catalyst precursors for the ploymerization of ethylene and propylene" J. Organomet. Chem. (1998), 568(1–2), 87–112.

Chemical Abstracts, vol. 117, No. 10, Sep. 7, 1992, Columbus, Ohio, US, Abstract No. 91047, Norihide Inoue et al., "Syndiotactic polypropylene prepared with metallocene catalysts".

* cited by examiner

Primary Examiner—Porfirio Nazario-Gonzalez
(74) Attorney, Agent, or Firm—Burns, Doane, Swecker & Mathis, L.L.P.

(57) ABSTRACT

There are herein disclosed a novel metallocene compound represented by the formula [1] and a process for preparing a polyolefin comprising the step of polymerizing an olefin in a catalytic system including the metallocene compound. The metallocene compound of the present invention particularly permits the preparation of a polyolefin having a high stereoregularity and a low molecular weight, and it is industrially extremely valuable:

formula [1]

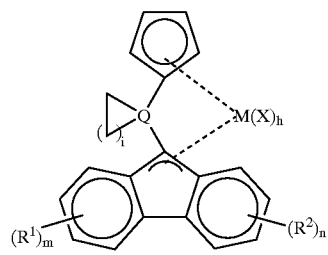

Figure 1:
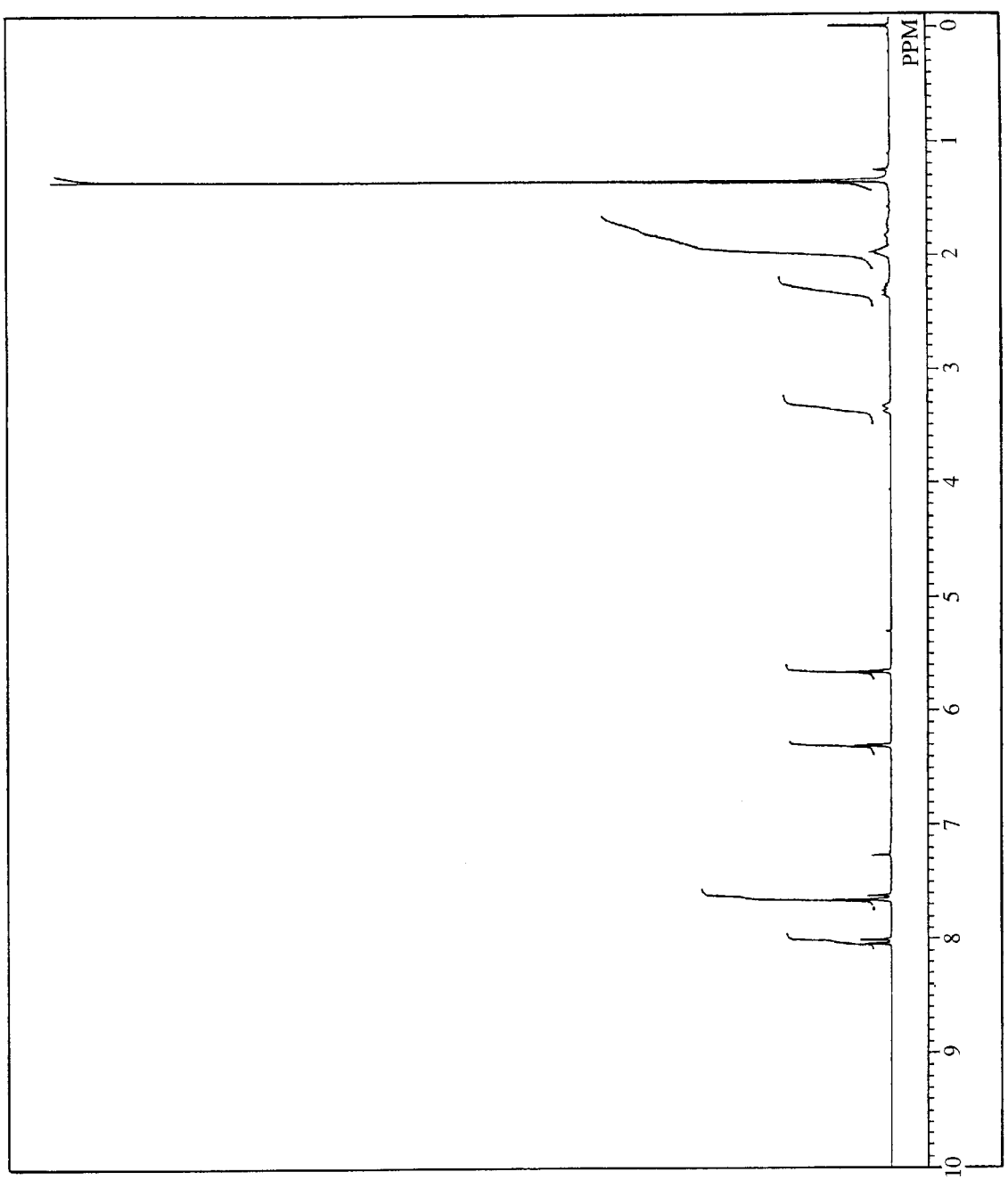

wherein $R^1$ and $R^2$ are each selected from the group consisting of an alkyl group, an aryl group and a silicon-containing alkyl group; M is a metal selected from the group IV of the periodic table; Q is carbon or silicon; X is a halogen, an alkyl group or an anionic ligand, and they may be selected so as to be the same or a combination of different ones; i is an integer of 1 to 10; n is an integer of 1 to 4; m is an integer of 0 to 4; and h is an integer of 1 to 3.

12 Claims, 1 Drawing Sheet

METALLOCENE COMPOUND, AND PROCESS FOR PREPARING POLYOLEFIN BY USING IT

BACKGROUND OF THE INVENTION (1) Field of the Invention

The present invention relates to a novel metallocene compound, and a process for preparing a polyolefin polymerizing an olefin by the use of this metallocene compound. More specifically, it relates to a metallocene compound having a specific structure and a process for preparing a polyolefin comprising the step of polymerizing an olefin by the use of the metallocene compound.

(2) Description of the Prior Art

As homogeneous catalysts for olefin polymerization, catalytic systems containing the so-called metallocene compound are well known.

Processes for polymerizing olefins by the use of a catalytic system containing a conventional metallocene compound have been improved from various angles.

In particular, a method for the stereoregular polymerization of an α-olefin has been variously improved since a report was made by W. Kaminsky et al. [Angew. Chem., Vol. 97, p. 507 (1985)].

As an improved example of such a method, there has been reported a metallocene compound having a C2 symmetrical structure in which some of hydrogen atoms on a cyclopentadienyl group constituting a ligand moiety of the metallocene compound are replaced with alkyl groups, and it has been prevalently attempted to improve the stereoregularity of an isotactic polymer obtained from the above-mentioned metallocene compound [Yamazaki et al., Chemistry Letters, p. 1853 (1989), and Japanese Patent Application Laid-Open No. 268307/1992].

Furthermore, as similar attempts, many researches have been reported in which the stereoregularity of an olefin polymer is to be improved by a catalytic system including a metallocene compound which has an ethylenebisindenyl derivative having the C2 symmetrical structure as a ligand [e.g., Organometallics, Vol. 13, p. 954 (1994), J. Organmet. Chem., Vol. 288, p. 63 (1985) and the like].

On the other hand, J. A. Ewen has found that an α-olefin can be polymerized in a syndiotactic stereoregularity by a catalytic system containing a metallocene compound having a Cs symmetrical structure in which a cyclopentadienyl group and a fluorenyl group are linked with dimethylmethane bridge [J. Am. Chem. Soc., Vol. 110, p. 6255 (1988)]. In order to improve this metallocene compound, it has been attempted to further control the stereoregularity by introducing a 2,7-di-tert-butylfluorenyl group in place of the fluorenyl group (Japanese Patent Application Laid-Open No. 69394/1992).

However, it is difficult to synthesize a syndiotactic α-olefin polymer having a high stereoregularity and a low molecular weight by the use of the metallocene compound having the Cs symmetrical structure under practical conditions of, for example, using a large amount of hydrogen, and accordingly it has been desired to further improve the metallocene compound.

SUMMARY OF THE INVENTION

For the purpose of solving the above-mentioned problems, the present inventors have intensively investigated on a metallocene compound having a novel structure capable of synthesizing an α-olefin polymer and a polymerization process in which this metallocene compound is used, and in consequence, the present invention has been completed.

That is to say, the first aspect of the present invention is directed to a novel metallocene compound represented by the formula [1]

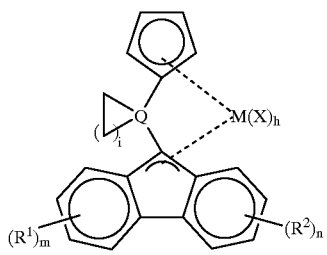

formula [1]

wherein $R^1$ and $R^2$ are each selected from the group consisting of an alkyl group, an aryl group and a silicon-containing alkyl group; M is a metal selected from the group IV of the periodic table; Q is carbon or silicon; X is a halogen, an alkyl group or an anionic ligand, and they may be selected so as to be the same or a combination of different ones; i is an integer of 1 to 10; n is an integer of 1 to 4; m is an integer of 0 to 4; and h is an integer of 1 to 3.

The second aspect of the present invention is directed to a process for preparing a polyolefin which comprises the step of polymerizing an olefin by the use of a catalytic system containing a metallocene compound containing represented by the formula [1].

DESCRIPTION OF THE PREFERRED EMBODIMENTS

In the present invention, $R^1$ and $R^2$ of the formula [1] are each selected from the group consisting of an alkyl group, an aryl group and a silicon-containing alkyl group.

The above-mentioned alkyl group is preferably an alkyl group having 1 to 20 carbon atoms, and typical examples of the alkyl group include methyl, ethyl, n-propyl, isopropyl, 2-methylpropyl, tert-butyl, cyclohexyl, norbornyl and menthyl.

The above-mentioned aryl group is preferably an aryl group having 6 to 20 carbon atoms, and typical examples of the aryl group include phenyl, tolyl and naphthyl.

The above-mentioned silicon-containing alkyl group is preferably a silicon-containing alkyl group having 1 to 20 carbon atoms, and typical examples of the silicon-containing alkyl group include trimethylsilyl and dimethylethylsilyl.

Furthermore, the substitutional position of each of $R^1$ and $R^2$ may be any position of the 1-position to 4-position, or the 5-position to 8-position of fluorene; n is in the range of 1 to 4; and m is in the range of 0 to 4.

In the present invention, Q is carbon or silicon, and a cycloalkyl group is formed in which i is in the range of 1 to 10.

Examples of the cycloalkyl group which can be constituted herein include cyclopropylidene, cyclobutylidene, cyclopentylidene, cyclohexylidene, cycloheptylidene, cyclodimethylenesilylene, cyclotrimethylenesilylene, cyclotetramethylenesilylene, cyclopentamethylenesilylene and cycloheptamethylenesilylene.

In the present invention, M of the formula [1] is a metal selected from the group 4 of the periodic table, and examples of M include titanium, zirconium and hafnium.

X of the formula [1] is a halogen, an alkyl group or an anionic ligand, and they may be selected so as to be the same or a combination of different ones.

Typical examples of the halogen include fluorine, chlorine, bromine and iodine.

The alkyl group is preferably an alkyl group having 1 to 20 carbon atoms, and its typical examples include methyl, ethyl, butyl, isopropyl and tert-butyl.

Typical examples of the anionic ligand include organic phosphorus compounds such as trimethylphosphine, triethylphosphine, triphenylphosphine and diphenylmethylphosphine; alkoxy groups such as methoxy, tert-butoxy and phenoxy; and ethers such as tetrahydrofuran (hereinafter referred to as "THF"), diethyl ether, dioxane and 1,2-dimethoxyethane.

Among them, Xs may be the same or a combination of different ones.

In the present invention, examples of the ligand which is a precursor of the metallocene compound represented by the formula [1] include 1-cyclopentadienyl-1-(2,7-ditert-butylfluorenyl)cyclopropane, 1-cyclopentadienyl-1-(2,7-di-tert-butylfluorenyl)cyclobutane, 1-cyclopentadienyl-1-(2,7-di-tert-butylfluorenyl)cyclopentane, 1-cyclopentadienyl-1-(2,7-di-tert-butylfluorenyl)cyclohexane, 1-cyclopentadienyl-1-(2,7-di-tert-butylfluorenyl)cycloheptane, 1-cyclopentadienyl-1-(3,6-di-tert-butylfluorenyl)cyclopropane, 1-cyclopentadienyl-1-(3,6-di-tert-butylfluorenyl)cyclobutane, 1-cyclopentadienyl-1-(3,6-di-tert-butylfluorenyl)cyclopentane, 1-cyclopentadienyl-1-(3,6-di-tert-butylfluorenyl)-cyclohexane, 1-cyclopentadienyl-1-(3,6-di-tert-butylfluorenyl)cycloheptane, 1-cyclopentadienyl-1-(2,7-di(trimethylsilyl)fluorenyl)cyclopropane, 1-cyclopentadienyl-1-(2,7-di(trimethylsilyl)fluorenyl)cyclobutane, 1-cyclopentadienyl-1-(2,7-di(trimethylsilyl)fluorenyl)cyclopentane, 1-cyclopentadienyl-1-(2,7-di(trimethylsilyl)fluorenyl)cyclohexane, 1-cyclopentadienyl-1-(2,7-di(trimethylsilyl)fluorenyl)cycloheptane, 1-cyclopentadienyl-1-(2,7-diphenylfluorenyl)cyclopropane, 1-cyclopentadienyl-1-(2,7-diphenylfluorenyl)cyclobutane, 1-cyclopentadienyl-1-(2,7-diphenylfluorenyl)cyclopentane, 1-cyclopentadienyl-1-(2,7-diphenylfluorenyl)cyclohexane, 1-cyclopentadienyl-1-(2,7-diphenylfluorenyl)cycloheptane, cyclopentadienyl-(2,7-di-tert-butylfluorenyl)cyclodimethylene silane, cyclopentadienyl-(2,7-di-tert-butylfluorenyl)cyclotrimethylene silane, cyclopentadienyl-(2,7-di-tert-butylfluorenyl)cyclotetramethylene silane, cyclopentadienyl-(2,7-di-tert-butylfluorenyl)cyclopentamethylene silane, cyclopentadienyl-(2,7-di-tert-butylfluorenyl)cycloheptamethylene silane, cyclopentadienyl-(3,6-di-tert-butylfluorenyl)cyclodimethylene silane, cyclopentadienyl-(3,6-di-tert-butylfluorenyl)-cyclotrimethylene silane, cyclopentadienyl-(3,6-di-tert-butylfluorenyl)cyclotetramethylene silane, cyclopentadienyl-(3,6-di-tert-butylfluorenyl)cyclopentamethylene silane, cyclopentadienyl-(3,6-di-tert-butylfluorenyl)cycloheptamethylene silane, cyclopentadienyl-(2,7-di(trimethylsilyl)fluorenyl)cyclodimethylene silane, cyclopentadienyl-(2,7-di(trimethylsilyl)fluorenyl)cyclotrimethylene silane, cyclopentadienyl-(2,7-di(trimethylsilyl)fluorenyl)cyclotetramethylene silane, cyclopentadienyl-(2,7-di(trimethylsilyl)fluorenyl)cyclopentamethylene silane, cyclopentadienyl-(2,7-di(trimethylsilyl)fluorenyl)cycloheptamethylene silane, cyclopentadienyl-(2,7-diphenylfluorenyl)cyclodimethylene silane, cyclopentadienyl-(2,7-diphenylfluorenyl)cyclotrimethylene silane, cyclopentadienyl-(2,7-diphenylfluorenyl)cyclotetramethylene silane, cyclopentadienyl-(2,7-diphenylfluorenyl)cyclopentamethylene silane and cyclopentadienyl-(2,7-diphenylfluorenyl) cycloheptamethylene silane.

In the present invention, no particular restriction is put on a preparation method of the ligand which is the precursor of the metallocene compound represented by the formula [1], but for example, it can be synthesized in accordance with the following formula [2] or [3].

formula [2]

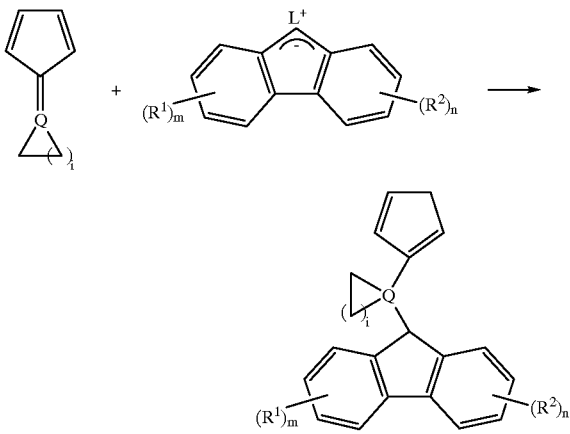

wherein $R^1$ and $R^2$ are each selected from the group consisting of an alkyl group, an aryl group and a silicon-containing alkyl group; Q is carbon or silicon; L is an alkali metal; i is an integer of 1 to 10; n is an integer of 1 to 4; and m is an integer of 0 to 4.

formula [3]

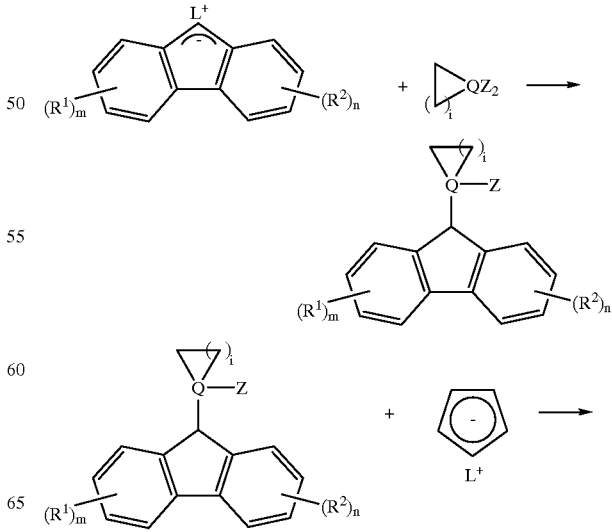

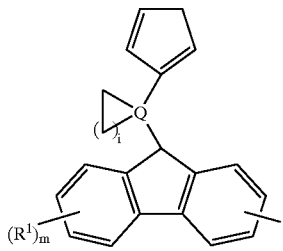

wherein $R^1$ and $R^2$ are each selected from the group consisting of an alkyl group, an aryl group and a silicon-containing alkyl group; Q is carbon or silicon; L is an alkali metal; Z is a halogen; i is an integer of 1 to 10; n is an integer of 1 to 4; and m is an integer of 0 to 4.

Examples of the alkali metal which can be particularly preferably used in the above-mentioned reaction include lithium, sodium and potassium, and examples of the halogen include fluorine, chlorine, bromine and iodine.

The above-mentioned reaction can be carried out in the temperature range of −80° C. to 200° C. in an organic solvent, for example, an aliphatic hydrocarbon such as pentane, hexane, heptane, cyclohexane or decalin, an aromatic hydrocarbon such as benzene, toluene or xylene, or an ether such as THF, diethyl ether, dioxane or 1,2-dimethoxy ethane.

Furthermore, the ligand which is the precursor of the metallocene compound of the formula [1] obtained by the reaction of the formula [2] or [3] is brought into contact with an alkali metal hydride or an organic alkali metal in an organic solvent such as the above-mentioned aliphatic hydrocarbon, aromatic hydrocarbon or ether in the temperature range of −80° C. to 200° C., thereby forming a di-alkali metal salt.

Examples of the alkali metal which can be used in the above-mentioned reaction include lithium, sodium and potassium, and examples of the alkali metal hydride include sodium hydride and potassium hydride.

The metallocene compound of the formula [1] can be synthesized by reacting the di-alkali metal salt of the ligand with a halide of a metal selected from the group 4 of the periodic table.

Typical examples of the halide of the metal selected from the group 4 of the periodic table include fluorides, chlorides, bromides and iodides of trivalent and tetravalent titaniums, complexes of these compounds and ethers such as THF, diethyl ether, dioxane and 1,2-dimethoxyethane, tetrafluoride, tetrachloride, tetrabromide and tetraiodide of zirconium and ether complexes thereof, and tetrafluoride, tetrachloride, tetrabromide and tetraiodide of hafnium and ether complexes thereof.

The reaction of the di-alkali metal salt with the halide of the metal in the group 4 of the periodic table can be carried out preferably in an organic solvent in the reaction temperature range of −80° C. to 200° C. by using these material preferably in equimolar amounts.

Examples of the preferably usable organic solvent include aliphatic hydrocarbons such as pentane, hexane, heptane, cyclohexane and decalin, aromatic hydrocarbons such as benzene, toluene and xylene, ethers such as THF, diethyl ether, dioxane and dimethoxy ethane, and halogenated hydrocarbons such as dichloromethane and chloroform.

Typical examples of the metallocene compound represented by the formula [1] for use in the present invention include, but are not limited to, cyclopropylidene (cyclopentadienyl) (2,7-di-tert-butylfluorenyl)zirconium dichloride, cyclobutylidene(cyclopentadienyl) (2,7-di-tert-butylfluorenyl)zirconium dichloride, cyclopentylidene (cyclopentadienyl) (2,7-di-tert-butylfluorenyl)zirconium dichloride, cyclohexylidene(cyclopentadienyl) (2,7-di-tert-butylfluorenyl)zirconium dichloride, cycloheptylidene (cyclopentadienyl) (2,7-di-tert-butylfluorenyl)zirconium dichloride, cyclopropylidene(cyclopentadienyl) (3,6-di-tert-butylfluorenyl)zirconium dichloride, cyclobutylidene (cyclopentadienyl) (3,6-di-tert-butylfluorenyl)zirconium dichloride, cyclopentylidene(cyclopentadienyl) (3,6-di-tert-butylfluorenyl)zirconium dichloride, cyclohexylidene (cyclopentadienyl) (3,6-di-tert-butylfluorenyl)zirconium dichloride, cycloheptylidene(cyclopentadienyl) (3,6-di-tert-butylfluorenyl)zirconium dichloride, cyclopropylidene (cyclopentadienyl) (2,7-di(trimethylsilyl)fluorenyl) zirconium dichloride, cyclobutylidene(cyclopentadienyl) (2,7-di(trimethylsilyl)fluorenyl)zirconium dichloride, cyclopentylidene(cyclopentadienyl) (2,7-di(trimethylsilyl) fluorenyl)zirconium dichloride, cyclohexylidene (cyclopentadienyl) (2,7-di(trimethylsilyl)fluorenyl) zirconium dichloride, cycloheptylidene(cyclopentadienyl) (2,7-di(trimethylsilyl)fluorenyl)zirconium dichloride, cyclopropylidene(cyclopentadienyl)(2,7-diphenylfluorenyl) zirconium dichloride, cyclobutylidene(cyclopentadienyl) (2,7-diphenylfluorenyl)zirconium dichloride, cyclopentylidene(cyclopentadienyl) (2,7-diphenylfluorenyl) zirconium dichloride, cyclohexylidene(cyclopentadienyl) (2,7-diphenylfluorenyl)zirconium dichloride, cycloheptylidene(cyclopentadienyl) (2,7-diphenylfluorenyl) zirconium dichloride, cyclodimethylenesilylene (cyclopentadienyl) (2,7-di-tert-butylfluorenyl)zirconium dichloride, cyclotrimethylenesilylene(cyclopentadienyl) (2,7-di-tert-butylfluorenyl)zirconium dichloride, cyclotetramethylenesilylene(cyclopentadienyl) (2,7-di-tertbutylfluorenyl)zirconium dichloride, cyclopentamethylenesilylene(cyclopentadienyl) (2,7-di-tert-butylfluorenyl)zirconium dichloride, cycloheptamethylenesilylene(cyclopentadienyl) (2,7-di-tert-butylfluorenyl)zirconium dichloride, cyclodimethylenesilylene(cyclopentadienyl) (3,6-di-tertbutylfluorenyl)zirconium dichloride, cyclotrimethylenesilylene(cyclopentadienyl) (3,6-di-tert-butylfluorenyl)zirconium dichloride, cyclotetramethylenesilylene(cyclopentadienyl)(3,6-di-tert-butylfluorenyl)zirconium dichloride, cyclopentamethylenesilylene(cyclopentadienyl) (3,6-di-tert-butylfluorenyl)zirconium dichloride, cyclopentamethylenesilylene(cyclopentadienyl) (3,6-di-tert-butylfluorenyl)zirconium dichloride, cyclodimethylenesilylene(cyclopentadienyl) (2,7-di (trimethylsilyl)fluorenyl)zirconium dichloride, cyclotrimethylenesilylene(cyclopentadienyl) (2,7-di (trimethylsilyl)fluorenyl)zirconium dichloride, cyclotetramethylenesilylene(cyclopentadienyl) (2,7-di (trimethylsilyl)fluorenyl)zirconium dichloride, cyclopentamethylenesilylene(cyclopentadienyl) (2,7-di (trimethylsilyl)fluorenyl)zirconium dichloride, cycloheptamethylenesilylene(cyclopentadienyl) (2,7-di (trimethylsilyl)fluorenyl)zirconium dichloride, cyclodimethylenesilylene(cyclopentadienyl) (2,7-diphenylfluorenyl)zirconium dichloride, cyclotrimethylenesilylene(cyclopentadienyl) (2,7-diphenylfluorenyl)zirconium dichloride, cyclotetramethylenesilylene(cyclopentadienyl) (2,7-diphenylfluorenyl)zirconium dichloride, cyclopentamethylenesilylene(cyclopentadienyl) (2,7- diphenylfluorenyl)zirconium dichloride and cycloheptamethylenesilylene(cyclopentadienyl) (2,7-diphenylfluorenyl)zirconium dichloride.

In addition, the metallocene compounds of the present invention also include metallocene compounds in which a part or all of the chlorine atoms are replaced with other substituents. Examples of such metallocene compounds include a metallocene compound in which chlorine is replaced with bromine, iodine or fluorine, a metallocene compound in which the halogen is replaced with an alkyl group such as a methyl group, a metallocene compound in which the halogen is replaced with trimethylphosphine, a metallocene compound in which the halogen is replaced with an alkoxy group such as a methoxy group, and a metallocene compound which is coordinated with THF.

In addition, the present invention can cover the above-mentioned metallocene compounds in which zirconium is replaced with titanium or hafnium.

Examples of the olefin, which is to be polymerized in the presence of the catalytic system including the metallocene compound represented by the formula [1] in the present invention, include α-olefins (inclusive of ethylene) having 2 to 20 carbon atoms, preferably α-olefins having 2 to 10 carbon atoms. Typical examples of the olefins include ethylene, propylene, 1-butene, 3-methyl-1-butene, 1-pentene, 4-methyl-1-pentene, 1-hexene, vinylcyclohexane and styrene.

In this invention, moreover, the olefins further include dienes having 4 to 20 carbon atoms such as butadiene, 1,4-pentadiene, 1,5-hexadiene and 1,4-hexadiene.

In addition, the olefins in this invention further include cyclic olefins such as dicyclopentadiene, norbornene, methylnorbornene, tetracyclododecene and methyltetracyclododecene, and silicon-containing olefins such as allyltrimethylsilane and vinyltrimethylsilane.

These olefins may be homopolymerized singly or copolymerized in a combination of two or more thereof.

In the present invention, there can be used a cocatalyst which is usually used as an olefin polymerization catalyst together with the metallocene compound.

In the present invention, as an organic aluminoxane which can be used together for the polymerization of the olefin by the use of the metallocene compound represented by the formula [1], there can be used a compound represented by the formula [4] or [5]

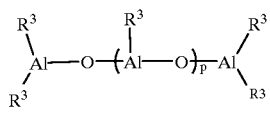

formula [4]

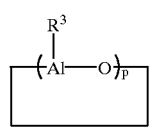

formula [5]

wherein $R^3$ may be the same or different, and it is an alkyl group having 1 to 6 carbon atoms, an aryl group having 6 to 18 carbon atoms, or hydrogen; and p is an integer of 2 to 50, preferably 10 to 35.

In the polymerization of the olefin, the ratio of the organic aluminoxane represented by the formula [4] or [5] to the metallocene compound represented by the formula [1] is usually such that a molar ratio of aluminum/the metallocene compound is in the range of 1 to 10,000.

In the case that the above-mentioned organic aluminoxane is used, an organic aluminum compound having 1 to 20 carbon atoms can be used together, and in this case, the employment of a relatively small amount of the aluminoxane permits obtaining a good performance. A ratio of the organic aluminum compound to the metallocene compound represented by the formula [1] is usually such that a molar ratio of aluminum/the metallocene compound is in the range of 1 to 10,000.

Examples of such an organic aluminum compound include trimethyl aluminum, triethyl aluminum, tripropyl aluminum, triisopropyl aluminum, tri-n-butyl aluminum, triisobutyl aluminum, tri-sec-butyl aluminum, dimethyl aluminum chloride, diethyl aluminum chloride, dipropyl aluminum chloride, diisopropyl aluminum chloride, di-n-butyl aluminum chloride, diisobutyl aluminum chloride and di-secbutyl aluminum chloride.

Furthermore, the metallocene compound represented by the formula [1] and the organic aluminoxane represented by the formula [4] or [5] which can be used in the present invention, when used, may be brought into contact with a carrier which is insoluble in an inert organic solvent of a hydrocarbon such as pentane, hexane, heptane, benzene or toluene.

Examples of the carrier include inorganic oxides and organic polymer which are insoluble in an inert organic solvent having a functional group.

In the present invention, as the inorganic oxide which can be used in the preparation of a solid catalyst component obtained by bringing the organic aluminoxane represented by the formula [4] or [5] or the methallocene compound into contact with the inorganic oxide, there can be preferably utilized an oxide having voids therein or an oxide having relatively large pores and hence a large surface area.

Examples of the oxide include $SiO_2$, $Al_2O_3$, $CaO$, $Na_2O$, $K_2$, $MgO$, $MnO_m$ (m is 1 or 2), $TiO_2$ and $ZrO_2$. In addition, hollow inorganic oxides and gels of oxides can also be utilized.

In general, the diameter of the inorganic oxide is preferably in the range of about 1 $\mu$m to about 0.1 mm.

Above all, an oxide including silica gel or alumina is preferable, because such a kind of oxide permits a large amount of the organic aluminoxane to be supported thereon.

Usually, the inorganic oxide is previously calcined before brought into contact with the organic aluminoxane, and the thus dried inorganic oxide is then used. However, the anhydrous inorganic oxide including 10% by weight or less of adsorbed water is also acceptable.

The above-mentioned solid catalyst component can be obtained by bringinging the organic aluminoxane for use in the present invention into contact with the inorganic oxide. That is to say, concretely, the solid catalyst component can be obtained by suspending the inorganic oxide in an alkane, an aromatic hydrocarbon, an ether or a halogenated hydrocarbon which is an organic solvent inert to the organic aluminoxane, and then mixing the resultant suspension with the organic aluminoxane at a temperature of 50 to 200° C.

In this case, the contact amount of the organic aluminoxane is at least in excess of a predetermined amount of the organic aluminoxane to be supported on the inorganic oxide, and it is 1.5 times or more, preferably twice or more as much as the predetermined amount of the organic aluminoxane. If this amount of the organic aluminoxane is less than 1.5 times, the sufficiently catalytic activity cannot be obtained inconveniently.

After the organic aluminoxane has been brought into contact with the inorganic oxide, the unreacted organic aluminoxane is separated from the obtained solid catalyst component. No particular restriction is put on a technique for this separation, but there can be utilized conventional filtration or decantation in which a supernatant obtained by still standing is removed. The thus separated solid catalyst component may be further washed with an inert organic solvent, as needed.

Alternatively, the organic aluminoxane represented by the formula [4] or [5] in the present invention can be brought into contact with an organic polymer having a functional group to prepare the solid catalyst component, but examples of the functional group contained in this organic polymer include aldehyde, carboxyl, ketones, carboxycarbonyls (dicarboxylic anhydrides), esters, halogenated carbonyls, amides and imides.

Furthermore, as the organic polymer having the functional group which can be used in the present invention, there can be utilized the following polymers (1), (2) and (3).

(1) A polymer obtained by (co)polymerizing a monomer (s) having the functional group.

(2) A polymer obtained by grafting or graft-polymerizing a monomer having the functional group to a polymer having no functional group.

(3) A polymer obtained by modifying a polymer with a compound having the functional group or a precursor of the functional group.

These polymers will be described in more detail. Examples of the monomer having the functional group for use in the polymerization of the organic polymer of the above-mentioned (1) include, but are not limited to, acrylic acids such as methacrylic acid and acrylic acid; acrylates such as methyl methacrylate and methyl acrylate; acrylamides such as methacrylamide, acrylamide and crotonamide; vinyl compounds such as vinyl acetate, methylvinyl ketone, acryloyl chloride and acrylaldehyde; lactones such as β-propiolactone; lactams such as ε-caprolactam; isocyanates such as tetramethylene diisocyanate, hexamethylene diisocyanate and octamethylene diisocyanate; N-carboxyamino acid anhydrides such as β-benzylaspartic anhydride and 4-benzyloxazolid-2,5-dione; aminocarboxylic acids such as β-aminocaproic acid and ω-aminoundecanoic acid; carboxylic anhydrides such as maleic anhydride, itaconic anhydride, phthalic anhydride and pyromellitic anhydride; amines such as hexamethylenediamine, nonamethylenediamine and phenylenediamine; dicarboxylic acids such as adipic acid, maleic acid and itaconic acid; halofolmylic acids such as adipic acid dichloride and phthalic acid dichloride; esters such as dimethyl terephthalate; and alcohols and phenols such as ethylene glycol, propylene glycol, butanediol, hexamethylene glycol and bisphenol A.

The organic polymer of the above-mentioned (1) can be obtained by subjecting one of these monomers or a combination of two or more thereof, or a combination of any of the above-mentioned monomers and a monomer having no functional group, to polymerization or copolymerization such as radical polymerization, cationic polymerization, anionic polymerization, transition metal catalytic polymerization, ring opening polymerization, polyaddition reaction, addition condensation reaction or polycondensation reaction.

Examples of the monomer having no functional group include α-olefins, styrenes, epoxy group-containing monomers and ether group-containing monomers.

The organic polymer of the above-mentioned (2) obtained by grafting or graft-polymerizing the monomer having the functional group is an organic polymer obtained by grafting or graft-polymerizing a dicarboxylic acid or the like to a polymer having no functional group in accordance with a reaction such as radical reaction or the Friedel-Crafts reaction.

Examples of the above-mentioned polymer having no functional group include polyethylene, polypropylene, ethylene-propylene copolymer, polybutene, ethylene-butene copolymer, ethylene-propylene-butene copolymer, polyisobutene, polypentene, poly(4-methylpentene), polynorbornene, polybutadiene, polyisoprene, polystyrene, poly(α-methylstyrene), polyethylene oxide, polypropylene oxide, polytetrahydrofuran and polysiloxane.

The above-mentioned polymer can be obtained by grafting or graft-polymerizing, for example, any of acrylic acids such as methacrylic acid and acrylic acid; acrylates such as methyl methacrylate, 3-methacryloxypropyltrimethoxysilane and methyl acrylate; acrylamides such as methacrylamide, acrylamide and crotoneamide; vinyl compounds such as vinyl acetate, methyl vinyl ketone, acryloyl chloride and acrylaldehyde; haloformyls such as acetyl chloride, adipic acid dichloride and phthalic acid dichloride; carboxylic anhydrides such as acetic anhydride, maleic anhydride and itaconic anhydride; and dicarboxylic acids such as maleic acid and itaconic acid, to a polymer having no functional group in accordance with the radical reaction, the Friedel-Crafts reaction or the like.

Furthermore, the polymer (3) obtained by modifying the polymer with the compound having the functional group or the precursor of the functional group is a partially modified organic polymer obtained by subjecting a polymer such as polyvinyl alcohol, polyvinyl chloride, polyvinylpyridine, nitrated polystyrene, polyacrylonitrile or cellulose to a reaction such as esterification reaction, oxidation reaction, reduction reaction or acylation reaction.

Preferable examples of the above-mentioned organic polymer having the functional group include polyolefins such as polyethylene and polypropylene obtained by grafting or graft-polymerizing maleic anhydride, itaconic anhydride, methacrylic acid, acrylic acid, methyl methacrylate and methyl acrylate in accordance with radical reaction.

In particular, grafted or graft polymerized polyolefins such as polyethylene and polypropylene obtained by grafting maleic anhydride are preferable because of easy synthesis.

As techniques for preparing the solid catalyst component by bringing the organic aluminoxane into contact with the organic polymer having the functional group for use in the present invention, there are the following methods (I), (II) and (III).

(I) A method of bringing the organic aluminoxane into contact with the organic polymer having the functional group dissolved in a heated inert organic solvent.

(II) A method of bringing the organic aluminoxane into contact with the organic polymer having the functional group suspended in an inert organic solvent.

(III) A method of bringing the organic aluminoxane into contact with the powdery organic polymer having the functional group.

The inert organic solvent which can be used here is an alkane, an aromatic hydrocarbon, an ether or a halogenated hydrocarbon compound, and it is preferably an alkane having 1 to 20 carbon atoms, an aromatic hydrocarbon compound having 6 to 20 carbon atoms, an ether having 2 to 20 carbon atoms, or a halogenated hydrocarbon having 1 to 20 carbon atoms. Typical examples of the alkane include pentane, heptane, octane, isobutane, neopentane, cyclopentane and decalin; examples of the aromatic hydrocarbon compound include benzene, toluene and xylene; examples of the ether include diethyl ether, tetrahydrofuran, 1,2-dimethoxyethane and dioxane; and examples of the halogenated hydrocarbon include dichloromethane and chloroform. Moreover, the inert organic solvent may be a mixture of some of these compounds.

In the method of the above-mentioned (I), the organic polymer having the functional group, which is insoluble in an inactive organic solvent at room temperature, is heated and dissolved in the inert organic solvent at a temperature of 40° C. to 250° C., preferably 60° C. to 200° C., and the resultant solution is then mixed with the organic aluminoxane, whereby both the components can be brought into contact with each other.

Then, a poor solvent is added to the solution which has been subjected to the contact treatment, thereby causing precipitation, and the resultant precipitate is collected by filtration. If necessary, the precipitate may be washed with a solvent prior to its use. The solvent is removed therefrom, and the precipitate may further be pulverized by a vibration mill, a ball mill or the like.

In the method of the above-mentioned (II), the organic polymer having the functional group is suspended in the inert organic solvent, and the resultant suspension is mixed with the organic aluminoxane at a temperature of –80° C. to 200° C., preferably –20° C. to 150° C., whereby both the components can be brought into contact with each other. The suspension may then be washed prior to its use. Afterward, a poor solvent may be added to the suspension which has been subjected to the contact treatment, and it may be then used.

Furthermore, the solvent may be removed from the suspension, and the solvent-free suspension is then pulverized by a vibration mill, a ball mill or the like prior to its use.

In the method of the above-mentioned (III), the powdery organic polymer having the functional group may be mixed with the organic aluminoxane substantially in the absence of any solvent at a temperature of –80° C. to 200° C., or preferably –20° C. to 150° C. by a mixing machine or a pulverizer such as a mixer or a mill, whereby these materials can be brought into contact with each other, and this mixture may be then used. The powder thus obtained may further be suspended in a poor solvent.

Moreover, the solid catalyst component obtained by any of the above-mentioned methods (I) to (III) which can be used in the present invention may be washed with an inert organic solvent as occasion demands.

A contact amount ratio between the organic aluminoxane and the organic polymer obtained by any of the above-mentioned methods (I) to (III) which can be used in the present invention is such that a mol number of aluminum contained in the organic aluminoxane is in the range of $1 \times 10^{-5}$ to 0.1 mol, preferably $1 \times 10^{-4}$ to 0.01 mol with respect to 1 g of the organic polymer.

The organic polymer contains the functional group for use in the synthesis of the solid catalyst component.

In the present invention, the ratio of the organic aluminoxane represented by the formula [4] or [5], or the solid catalyst component with respect to the metallocene compound represented by the formula [1] is such that a mol number (aluminum/a transition metal) of aluminum contained in the organic aluminoxane or the organic aluminoxane present in the solid catalyst component with respect to a mol number of the transition metal in the metallocene compound is in the range of 1 to 10000, preferably 10 to 2000.

The solid catalyst component can be obtained by bringing the organic aluminoxane into contact with the organic polymer having the functional group, or alternatively by bringing the organic aluminoxane into contact with an inorganic oxide.

When the olefin is polymerized with the metallocene compound represented by the formula [1] in the present invention, the metallocene compound to be used may be converted into a cationic compound, and an ionic compound which can produce a stable paired anionic species may be used. In this case, an organic aluminum compound is preferably used together.

Typical examples of the ionic compound include carbenium boranes, metal boranes and ammonium boranes such as triphenylcarbeniumtetrakis(pentafluorophenyl) borate, ferroceniumtetrakis(pentafluorophenyl) borate, N,N-dimethylammoniumtetrakis(pentafluorophenyl) borate, tri-n-butylammoniumtetrakis(pentafluorophenyl) borate, triethylammoniumtetrakis(phenyl) borate and tri-n-butylammoniumtetra(phenyl) borate.

In addition, for example, compounds exemplified in Japanese PCT Patent Application Laid-Open Nos. 501950/1989 and 502036/1989 can also be used.

The molar ratio of the ionic compound with respect to the metallocene compound is such that the ionic compound/the metallocene compound is in the range of 0.1 to 10.

Furthermore, the above-mentioned organic aluminum compound which can be used herein has 1 to 20 carbon atoms, and examples of the organic aluminum compound include trimethylaluminum, triethylaluminum, tripropylaluminum, triisopropylaluminum, tri-n-butylaluminum, triisobutylaluminum, tri-sec-butylaluminum, dimethylaluminum chloride, diethylaluminum chloride, dipropylaluminum chloride, diisopropylaluminum chloride, di-n-butylaluminum chloride, diisobutylaluminum chloride and di-sec-butylaluminum chloride.

The molar ratio of the organic aluminum compound with respect to the metallocene compound is such that the organic aluminum compound/the metallocene compound is in the range of 1 to 10,000.

In the present invention, the polymerization of the olefin can be carried out by any of a usual solvent polymerization, a bulk polymerization and a gaseous phase polymerization. A polymerization temperature is usually in the range of –100 to 200° C., preferably –20 to 100° C., and no particular restriction is put on a polymerization pressure, but the preferable polymerization pressure is in the range of atmospheric pressure to 5 MPa gauge pressure. In the polymerization, hydrogen can be added to the polymerization system in order to decrease the molecular weight of the produced polymer, and the amount of hydrogen depends on the molecular weight of the desired polymer, but it is suitably in the range of 0.01 to 20 NL per kg of the olefin. The molecular weight of the polyolefin obtained by the present invention is preferably in the range of 1,000 to 100,000, more preferably 5,000 to 50,000, most preferably 5,000 to 40,000 in terms of a molecular weight Mw by GPC.

The practice of the process according to the present invention permits the preparation of a polyolefin having a high stereoregularity and a low molecular weight, and hence the process is industrially extremely valuable.

Next, the present invention will be described in detail in accordance with examples, but the scope of the present invention should not be limited to these examples at all.

EXAMPLE 1

[Synthesis of a metallocene compound]

(1) Cyclohexylfulvene 8.2 ml (100 mmol) of cyclopentadiene and 4.2 ml (40 mmol) of cyclohexanone were added to 40 ml of dehydrated methanol, and 5.0 ml (60 mmol) of pyrrolidine were then added dropwise at 0° C. Then, reaction was carried out at room temperature for 3 hours. Next, 3.8 ml of acetic acid were slowly added at 0° C., and 20 ml of water were further added, followed by extraction with diethyl ether. The resultant organic phase, after washed with water, was dried over magnesium sulfate, and the used solvent was then distilled off to obtain 5.95 g of a yellow liquid.

$^1$H-NMR spectrum (90 MHz, CDCl3) δ6.50(4H), 2.60 (4H), 1.66(6H)

(2) 1-cyclopentadienyl-1-(2,7-di-tert-butylfluorenyl) cyclohexane

To a THF (30 ml) solution including 5.0 g (18.6 mmol) of 2,7-di-tert-butylfluorene, a hexane solution (13.5 ml, 21.6 mmol) of n-butyllithium was added dropwise at −78° C. under nitrogen, followed by stirring at room temperature for 6 hours. Next, a THF (20 ml) solution including 3.42 g (23.4 mmol) of cyclohexylfulvene was added dropwise at 0° C. under a nitrogen atmosphere, followed by stirring at room temperature for 16 hours. The resultant reaction solution was decomposed with cold water, and then extracted with ether. The extract was dried over magnesium sulfate and then filtered, and the used solvent was removed from the filtrate under reduced pressure, thereby obtaining a solid. This solid was recrystallized from methanol to obtain 5.36 g of a colorless solid.

$^1$H-NMR spectrum (270 MHz, CDCl3) δ7.53(2H), 7.35–7.15(4H), 6.65–6.35, 5.93(3H), 3.91, 3.87(1H), 3.07, 2.92(2H), 1.90–0.90(10H), 1.32(18H)

(3) Cyclohexylidene(cyclopentadienyl) (2,7-di-tertbutylfluorenyl)zirconium dichloride 5.8 ml (5.8 mmol) of a diethyl ether solution of methyllithium were added dropwise under ice cooling under nitrogen to a THF (20 ml) solution including 1.0 g (2.36 mmol) of 1-cyclopentadienyl-1-(2,7-di-tert-butylfluorenyl) cyclohexane synthesized in the above-mentioned (2), followed by stirring at room temperature for 7 hours. Next, the THF was distilled off under nitrogen, and the resultant solid was washed with hexane and then dissolved in dichloromethane cooled to −78° C. To this solution, zirconium tetrachloride 2THF complex (0.81 g, 2.15 mmol) dissolved in dichloromethane was added at −78° C., and after stirring for 24, the temperature of the solution was slowly returned to room temperature.

Furthermore, this solution was filtered through cerite, and the resultant filtrate was concentrated to remove the solvent, followed by cooling at −30° C. The precipitated solid was washed with pentane, and then dried under reduced pressure to obtain 90 mg of a red solid.

$^1$H-NMR spectrum (270 MHz, CDCl3) δ8.02(2H), 7.65 (2H), 7.63(2H), 6.30(2H), 5.65(2H), 3.40–3.30(2H), 2.36–1.66(8H), 1.34(18H)

The $^1$H-NMR spectrum of the obtained metallocene compound is shown in FIG. 1.

FD-MS spectrum m/z=582–590 (M$^+$)
According to this spectrum, and FD-MS spectrum it was confirmed that the obtained compound was the desired metallocene compound.

EXAMPLE 2

In a 5-liter autoclave sufficiently purged with nitrogen were placed a toluene solution including 1.7 mg of a red solid obtained in Example 1 and methylaluminoxane (made by Albemal Co., Ltd.) in an amount of 25 mmol in terms of aluminum, and polymerization was then carried out at 70° C. for 1 hour in the presence of 0.325 NL of hydrogen and 1.5 kg of propylene. After the polymerization, propylene was purged, and the resultant polymer was dried at 80° C. for 6 hours under reduced pressure. The amount of the thus obtained polymer was 485 g, and its intrinsic viscosity [η] in tetralin at 135° C. was 0.504 dl/g. The molecular weight (Mw) by GPC was 36,200. The melting point (Tm) of the polymer by DSC was 138° C., and it was confirmed from the analytical results of infrared spectrum (IR) that the obtained polymer was a syndiotactic polypropylene.

EXAMPLE 3

The polymerization of propylene was carried out by the same procedure as in Example 2 except that methylaluminoxane in an amount of 25 mmol in terms of aluminum in Example 2 was replaced with 11 mg of triphenylcarbeniumtetrakis(pentafluorophenyl) borate and 128 mg of triisobutylaluminum. A polymer was obtained in an amount of 450 g, and it had [η]=0.51 dl/g, Tm=138° C., and Mw by GPC was 37,000 and it was confirmed from the analytical results of IR that the obtained polymer was a syndiotactic polypropylene.

EXAMPLE 4

The polymerization of propylene was carried out by the same procedure as in Example 2 except that, in place of methylaluminoxane in an amount of 25 mmol in terms of aluminum in Example 2, 1.7 mg of a metallocene compound used in Example 1 were supported on 90 mg of a solid component obtained by bringing 0.75 g of methylaluminoxane into contact with 1 g of 10 wt % maleic anhydride graft PP dissolved in xylene at 120° C. adding heptane to the mixture to cause precipitation, filtering, drying and then grinding; and 128 mg of triisobutylaluminum were used. The supporting procedure used here is disclosed in Japanese Patent Application Laid-open NO. 309911/1997.

A polymer was obtained in an amount of 545 g, and it had [η]=0.50 dl/g, and Tm=134° C. and Mw by GPC was 36,000 and it was confirmed from the analytical results of IR that the obtained polymer was a syndiotactic polypropylene.

Comparative Example 1

The polymerization of propylene was carried out by the same procedure as in Example 2 except that cyclohexylidene (cyclopentadienyl) (2,7-di-tert-butylfluorenyl) zirconium dichloride obtained in Example 1 was replaced with 0.82 mg of dimethylmethylene(cyclopentadienyl) (2,7-di-tertbutylfluorenyl)zirconium dichloride.

A polymer was obtained in an amount of 570 g, and it had [η]=0.68 dl/g, Tm=136° C. and Mw by GPC was 52,000 and it was confirmed from the analytical results of IR that the obtained polymer was a syndiotactic polypropylene.

Comparative Example 2

[Synthesis of a metallocene compound]

(1) 1-Cyclopentadienyl-1-(fluorenyl)cyclohexane

A hexane solution (20 ml, 32 mmol) of n-butyllithium was added dropwise to a THF (40 ml) solution including 5.0 g (30 mmol) of fluorene under nitrogen at −78° C., followed by stirring at room temperature for 6 hours.

Next, a THF (20 ml) solution including 5.8 g (39.7 mmol) of cyclohexylfulvene was added dropwise to the solution under a nitrogen atmosphere, followed by stirring at room temperature for 16 hours.

The resultant reaction solution was decomposed with cold water, and then extracted with ether. The extract was dried over magnesium sulfate and then filtered, and the used solvent was removed from the filtrate under reduced pressure, thereby obtaining a solid.

This solid was recrystallized from methanol to obtain 7.58 g of a colorless solid.

$^1$H-NMR spectrum (90 MHz, CDCl3) δ7.65(2H), 7.39–7.13(6H), 6.45, 5.84(3H), 3.94(1H), 2.98, 2.70(2H), 2.00–1.15(10H)

(2) Cyclohexylidene(cyclopentadienyl)(fluorenyl) zirconium dichloride

A hexane solution (2.3 ml, 4.6 mmol) of n-butyllithium was added dropwise under ice cooling under nitrogen to a THF (20 ml) solution including 1-cyclopentadienyl-1-(fluorenyl)cyclohexane (0.5 g, 1.6 mmol) synthesized in the above-mentioned (1), followed by stirring at room temperature for 7 hours.

Next, the THF was distilled off under nitrogen, and the resultant solid was washed with hexane and then dissolved in dichloromethane cooled to −78° C.

To this solution, zirconium tetrachloride 2THF complex (0.81 g, 2.15 mmol) dissolved in dichloromethane was added at −78° C., and after stirring for 24, the temperature of the solution was slowly returned to room temperature.

Furthermore, this solution was filtered through cerite, and the resultant filtrate was concentrated to remove the solvent, followed by cooling at −30° C. The precipitated solid was washed with pentane, and then dried under reduced pressure to obtain 65 mg of a red solid.

$^1$H-NMR spectrum (90 MHz, CDCl3) δ8.16(2H), 7.84–7.21(6H), 6.33(2H), 5.76(2H), 3.39–3.26(2H), 2.36–1.98(8H)

[Polymerization]

In a 5-liter autoclave sufficiently purged with nitrogen were placed a toluene solution including 1.7 mg of cyclohexylidene(cyclopentadienyl) (fluorenyl)zirconium dichloride obtained in Comparative Example 2 and methylaluminoxane (made by Albemal Co., Ltd.) in an amount of 25 mmol in terms of aluminum, and polymerization was then carried out at 70° C. for 1 hour in the presence of 0.325 NL of hydrogen and 1.5 kg of propylene.

After the polymerization, propylene was purged, and the resultant polymer was dried at 80° C. for 6 hours under reduced pressure.

This polymer was obtained in an amount of 310 g, and its intrinsic viscosity [η] in tetralin at 135° C. was 0.77 dl/g and Mw by GPC was 56,000. The melting point (Tm) of the polymer by DSC was 135° C., and it was confirmed from the analytical results of infrared spectrum (IR) that the obtained polymer was a syndiotactic polypropylene.

What is claimed is:

1. A process for preparing a polyolefin which comprises the step of polymerizing an olefin by the use of a system including a metallocene compound represented by the formula [1]

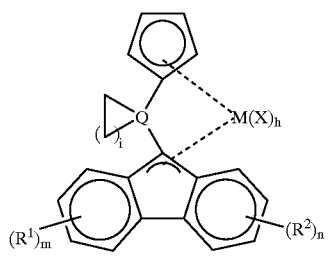

formula [1]

wherein $R^1$ and $R^2$ are each selected from the group consisting of an alkyl group, an aryl group and a silicon-containing alkyl group; M is a metal selected from the group IV of the periodic table; Q is carbon or silicon; X is a halogen, an alkyl group or an anionic ligand, and they may be selected so as to be the same or a combination of different ones; i is an integer of 4 to 10; n is an integer of 1 to 4; m is an integer of 0 to 4; and h is an integer of 1 to 3.

2. The process for preparing the polyolefin according to claim 1 wherein the metallocene compound represented by the formula [1] and an organic aluminoxane are used.

3. The process for preparing the polyolefin according to claim 1 wherein there is used a system including the metallocene compound represented by the formula [1], and an ionic compound which can convert the metallocene compound into a cationic compound to produce a stable anionic species.

4. The process for preparing the polyolefin according to claim 1 wherein an organic aluminum compound is further used together.

5. The process for preparing the polyolefin according to claim 1 wherein there are together used the metallocene compound represented by the formula [1], and an organic aluminoxane supported on a carrier which is insoluble in an inert organic solvent.

6. The process for preparing the polyolefin according to claim 5 wherein the carrier is a polymer having a functional group.

7. The process for preparing the polyolefin according to claim 6 wherein the polymer is a polypropylene to which a dicarboxylic anhydride is grafted.

8. The process for preparing the polyolefin according to claim 5 wherein the carrier is an inorganic oxide.

9. The process for preparing the polyolefin according to claim 1 wherein the polyolefin is a low-molecular weight polyolefin.

10. The process for preparing the polyolefin according to claim 1 wherein the polyolefin is a syndiotactic polypropylene.

11. The process according to claim 1 wherein, in the formula [1], $R^1$ and $R^2$ are tert-butyl groups at the 2 position and the 7 position of the formula [1], respectively; each of n and m is 1; i is 4; M is zirconium; Q is carbon; X is chlorine; and h is 2.

12. A process for preparing a polyolefin which comprises the step of polymerizing an olefin by the use of a system including a metallocene compound represented by the formula [1]

formula [1]

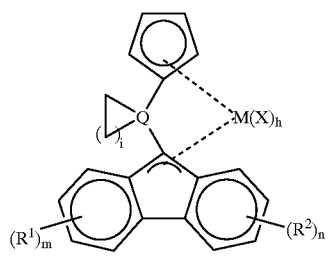

wherein $R_1$ and $R_2$ are each selected from the group consisting of an alkyl group, an aryl group and a silicon-containing alkyl group; M is a metal selected from the group IV of the periodic table; Q is carbon or silicon; X is a halogen, an alkyl group or an anionic ligand, and they may be selected so as to be the same or a combination of different ones; i is 4; n is an integer of 1 to 4; m is an integer of 0 to 4; and h is an integer of 1 to 3.

* * * * *